US00PP20534P2

(12) United States Plant Patent
Gargiulo

(10) Patent No.: US PP20,534 P2
(45) Date of Patent: Dec. 8, 2009

(54) GRAPEVINE PLANT NAMED '95-133'

(50) Latin Name: *Vitis vinifera*
Varietal Denomination: 95-133

(75) Inventor: Angel A. Gargiulo, Godoy Cruz (AR)

(73) Assignee: M. Caratan, Inc., Delano, CA (US)

( * ) Notice: Subject to any disclaimer, the term of this patent is extended or adjusted under 35 U.S.C. 154(b) by 0 days.

(21) Appl. No.: 12/286,830

(22) Filed: Oct. 2, 2008

(51) Int. Cl.
*A01H 5/00* (2006.01)

(52) U.S. Cl. ..... Plt./207

(58) Field of Classification Search ..... Plt./205, Plt./207

See application file for complete search history.

*Primary Examiner*—Susan B McCormick Ewoldt
(74) *Attorney, Agent, or Firm*—Jondle & Associates, P.C.

(57) ABSTRACT

A new and distinct grapevine plant particularly distinguished by having green, large, seedless berries, high vigor, berries with a very uniform skin color and medium productivity, is disclosed.

8 Drawing Sheets

Genus and species: *Vitis vinifera.*
Variety denomination: '95–133'.

BACKGROUND OF THE NEW PLANT

The present invention comprises a new and distinct cultivar of grapevine botanically known as *Vitis vinifera* and hereinafter referred to the cultivar name as grapevine '95–133'. The new cultivar originated from a cross conducted in May 1994 in Delano, Calif. between the proprietary grapevine plant '90–4981' (unpatented) and the proprietary male parent 'C.G. 88–552' (unpatented). The seeds produced from the cross were subsequently planted in in Delano, Calif. A single plant selection was chosen for further asexual propagation in January 2005 in Delano, Calif.

The new cultivar has been asexually reproduced repeatedly by vegetative cuttings in Delano, Calif. over a three and one-half year period. The present invention has been found to retain its distinctive characteristics through successive asexual propagations.

SUMMARY OF THE INVENTION

The following are the most outstanding and distinguishing characteristics of this new cultivar when grown under normal horticultural practices in Delano, Calif:.

1. Green, large seedless berries;
2. High vigor with medium productivity; and
3. Berries with a very uniform skin color.

DESCRIPTION OF THE PHOTOGRAPHS

This new grapevine plant is illustrated by the accompanying photographs which show clusters of fruit thereof, leaves, canes, tendrils and berries; the colors shown are as true as can be reasonably obtained by conventional photographic procedures. The photographs are taken from a plant about 3 and one-half years old, grown in a field in Delano, Calif. in July 2008 (at veraison) and in September 2008 (at harvest).

Figure 1:
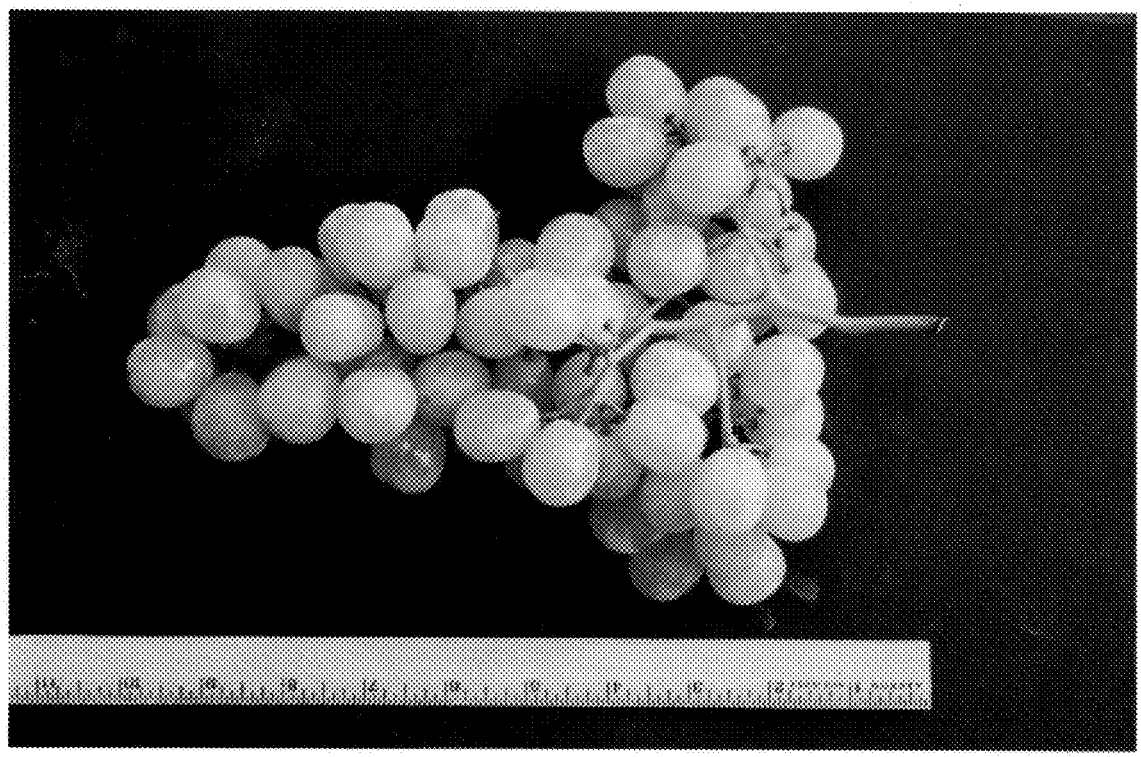
FIG. 1 shows a close-up of primary cluster of berries at harvest.
Figure 2:
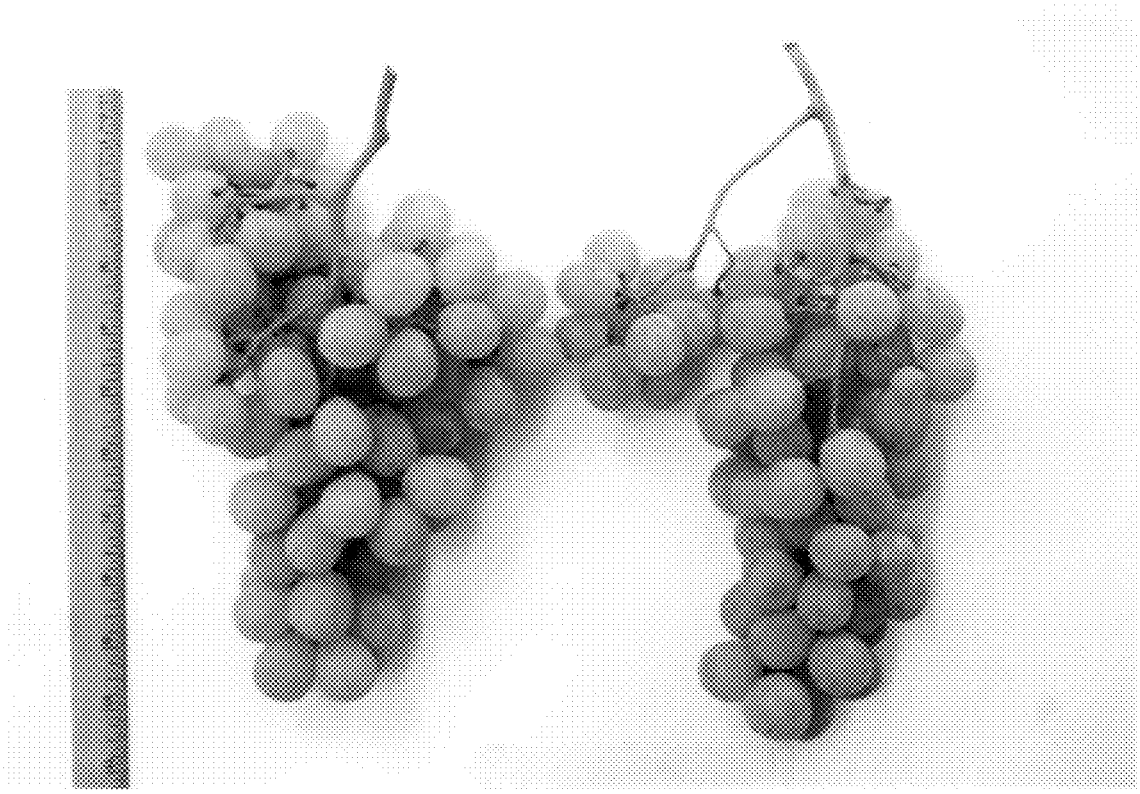
FIG. 2 shows a primary cluster of berries at harvest.
Figure 3:
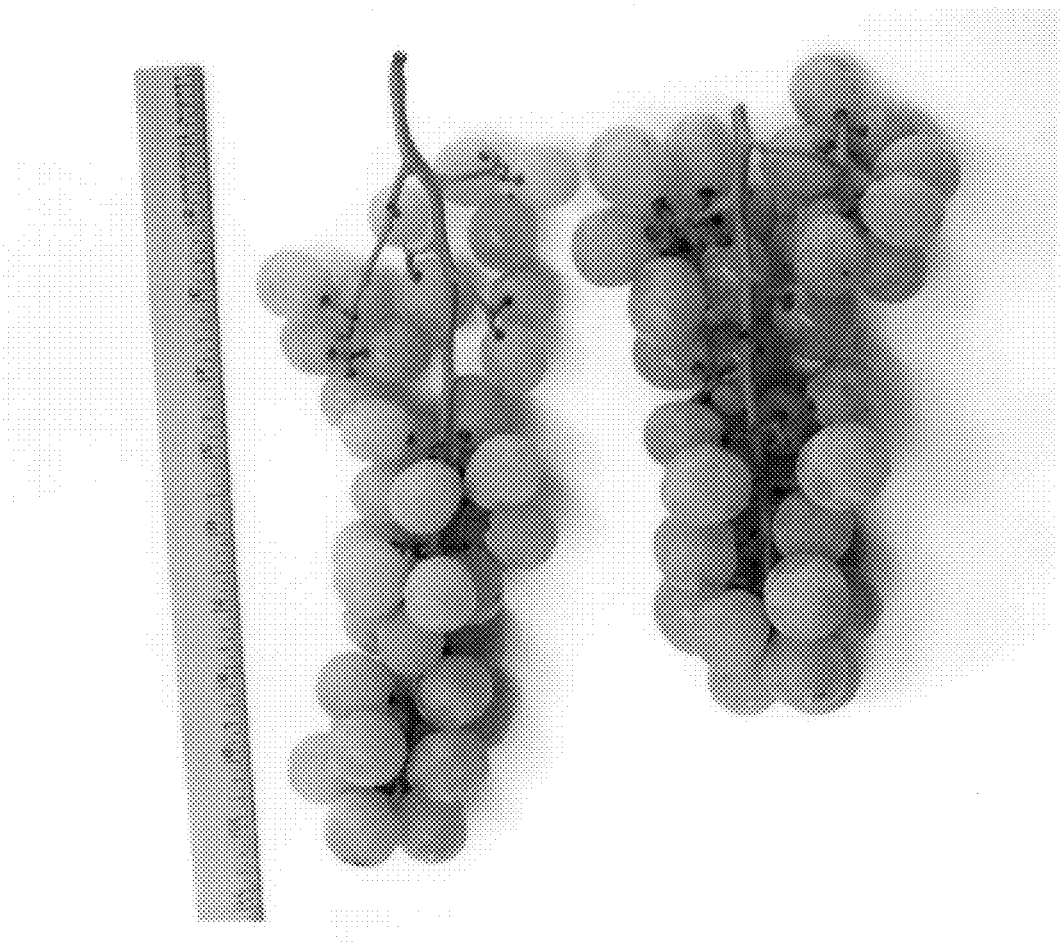
Figure 4:
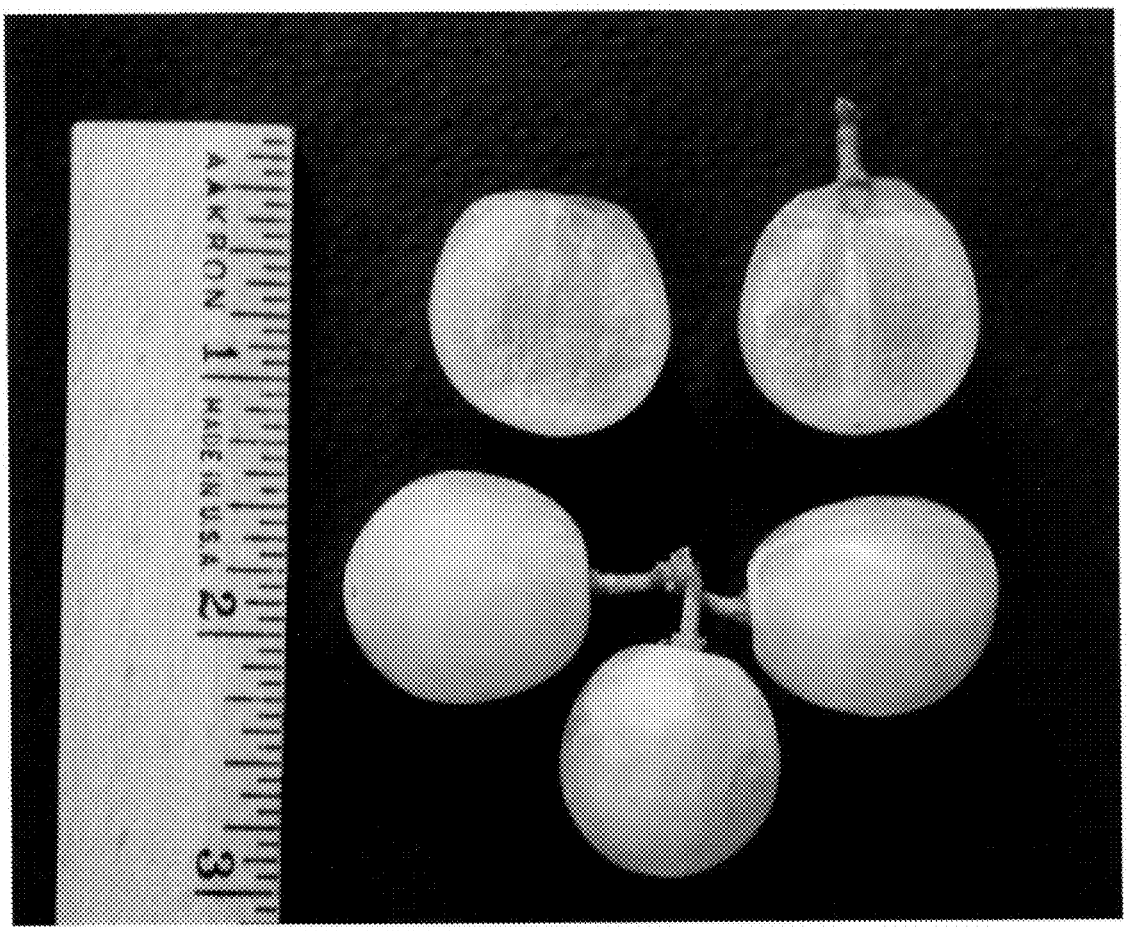
Figure 5:
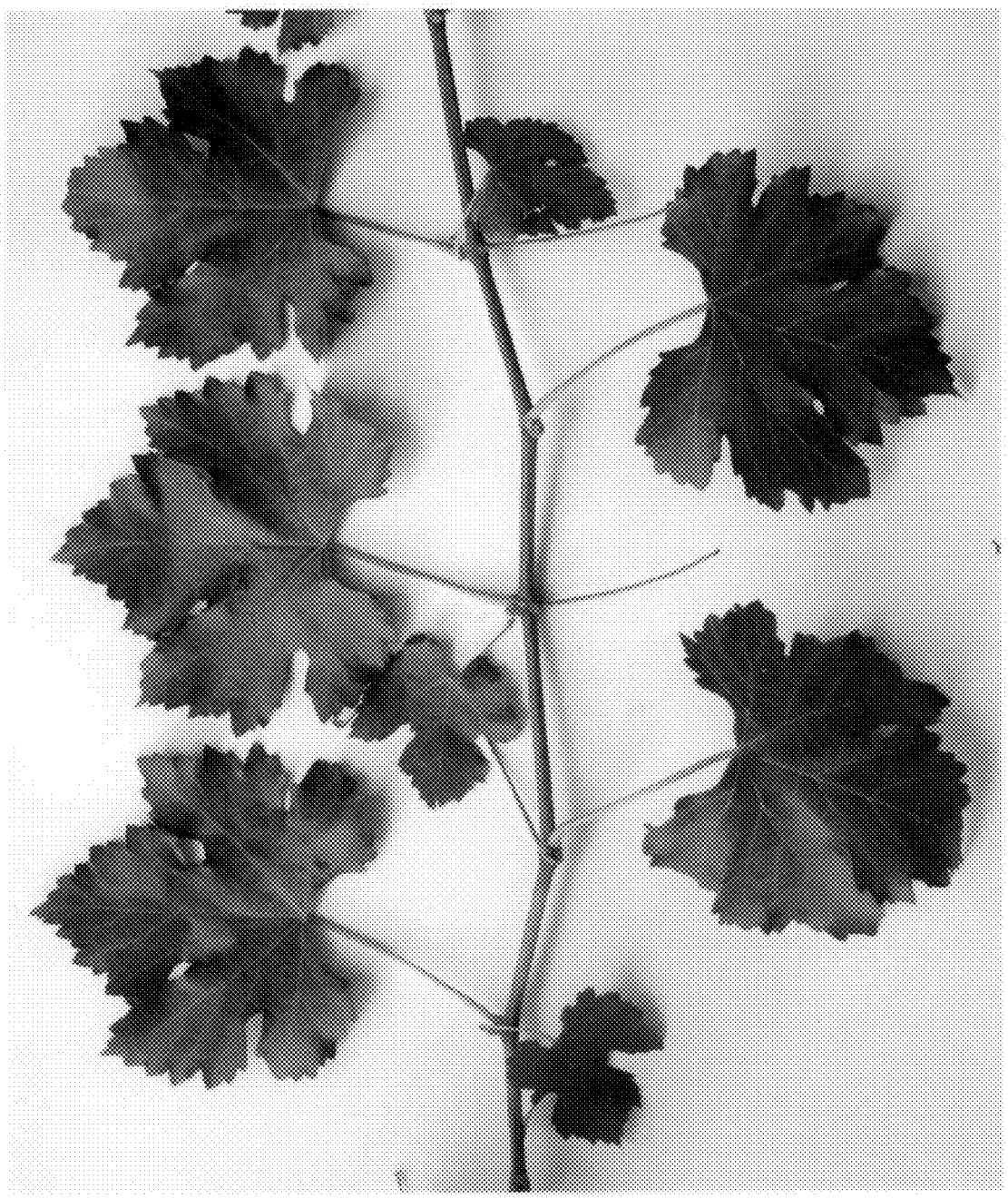
Figure 6:
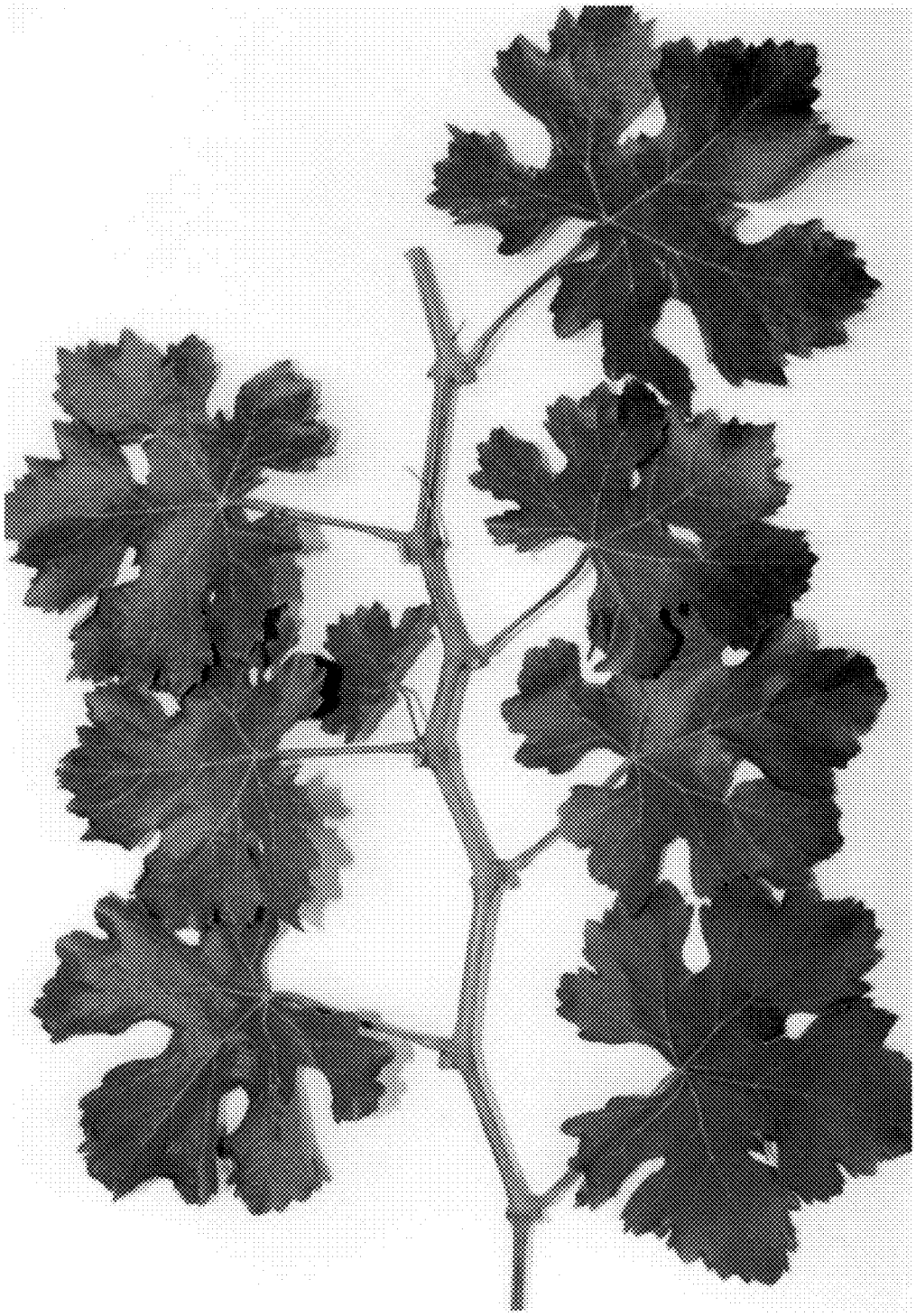
Figure 7:
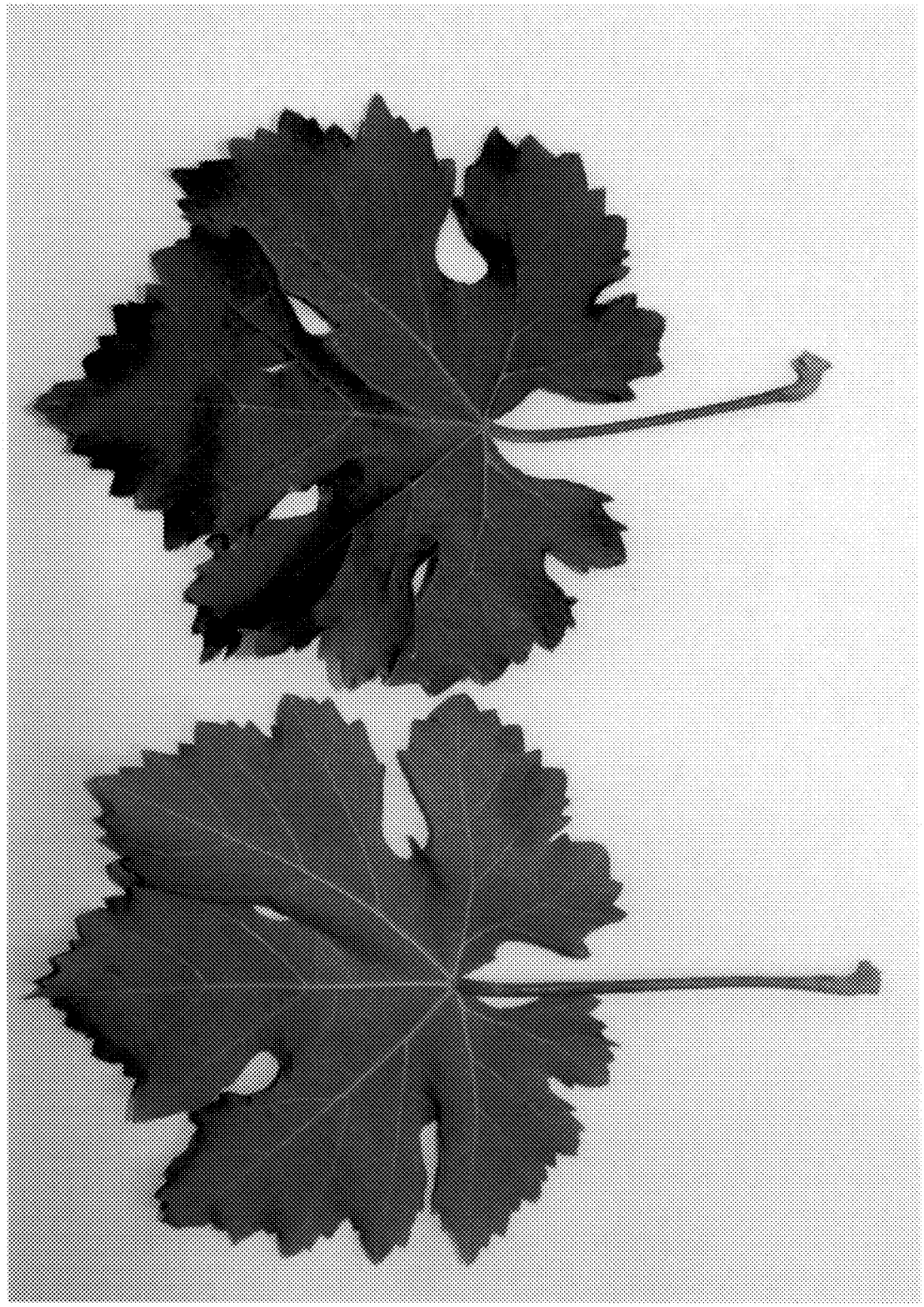
Figure 8:
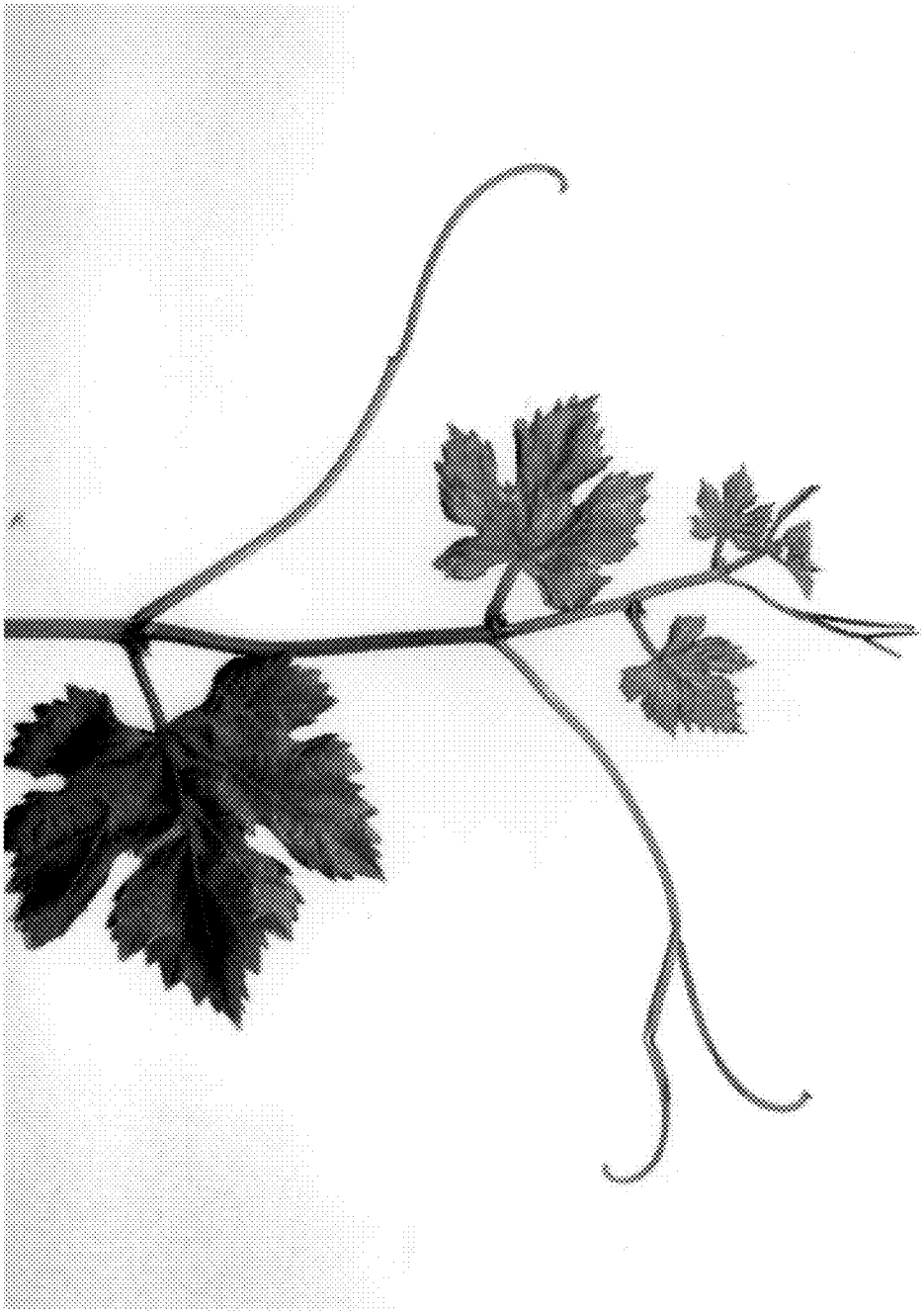

FIG. 3 shows a secondary cluster of berries at harvest.
FIG. 4 shows a close-up of the berries at harvest.
FIG. 5 shows a mature shoot (cane) at harvest.
FIG. 6 shows an immature shoot (cane) at veraison.
FIG. 7 shows a close-up of the mature leaves at veraison.
FIG. 8 shows a growing shoot tip at veraison.

DESCRIPTION OF THE NEW CULTIVAR

The following detailed description sets forth the distinctive characteristics of '95–133'. The data which defines these characteristics were collected from asexual reproductions carried out in Delano, Calif. The plant history was taken on 3 and one-half year old grapevines grown under field conditions in Delano, Calif. All color references were obtained under natural light. All major color code designations are by reference to Munsell Color Charts for Plant Tissues by Munsell Color, 617 Little Britain Rd., New Windsor, New York 12553–6148. Common color names are also occasionally employed. For the distribution of the tendrils, please refer to publication "Grape Varieties and Rootstock Varieties" by Pierre Galet, 1998 English Edition, Oenoplurimedia sarl, Chateau de Chaintre, 71570 Chaintre, France (where tendril distribution is intermittent, Os, 1s and 2s are referred to as follows: 0 is a node without a tendril; 2 refers to 2 nodes in a row with a tendril; and 1 is a single node with a tendril).

DETAILED BOTANICAL DESCRIPTION OF THE NEW PLANT

Classification:
- *Family.*—Vitaceae.
- *Botanical name.*—*Vitis vinifera.*
- *Variety name.*—95–133.

Plant:
- *Plant habit and growth.*—Trailing with some tendril attachment.
- *Height* (*at maturity*).—Cordon at 132.08 cm; canopy is 228.6 cm high.
- *Width* (*at maturity*).—Canopy is 241.3 cm wide.
- *Vigor.*—High.
- *Productivity.*—Medium.

*Rootstock.*—Own rootstock.

*Use.*—Fresh market table grapes.

Trunk:

*Diameter.*—8.13 cm.

*Surface texture.*—Coarse, rough.

*Color.*—Exposed surface is 5YR 7/2; non-exposed (when peeled) is 5YR 4/4.

Canes:

*Diameter* (*average*).—0.11 cm.

*Length* (*average*).—190.5 cm.

*Surface texture* (*both immature and mature canes*).—Smooth.

*Form* (*woody shoot cross section form*).—Pith in center with diaphragm at nodes.

*Color* (*mature*).—5R 6/6 at harvest, Sep. 9, 2008.

*Color* (*immature*).—2.5GY 8/6 at veraison, Jul. 2, 2008.

*Internode length* (*upper mature sun cane, average*).—8.89 cm.

Time of bud burst: Mar. 20, 2008

Tendrils:

*Form.*—Mostly with 2 branches, occasionally with a short (average 1.59 cm) branch on 1 branch.

*Size.*—General: Large Length (average): 23.50 cm on primary shoots and 12.6 cm on secondary shoots Diameter (average): Main branch: 0.3 cm Secondary branch: 0.2 cm.

*Texture and distribution.*—Smooth (no pubescence); tendril distribution is intermittent, mostly 0-0-0-0-2-0-2-0-0-2-0-2; occasionally 0-0-0-0-2-0-1-0-0-2-0-1 and 0-0-0-0-2-0-1-0-2-0-1-.

*Color*(*mature*).—2.5GY 8/6 for 8$^{th}$ tendril on node 12 from tip.

*Anthocynanin* (*mature*).—5R 5/4, more faded than on immature.

*Color.*—(*immature*).—2.5GY 7/8 for 3$^{rd}$ from tip.

*Anthocynanin* (*immature*).—5R 5/4, more intense as compared to mature tendrils.

Growing tips (young shoot):

*Pubescence.*—Slight.

*Color.*—2.5GY 6/8.

*Anthocynanin.*—Absent on 1$^{st}$ 3 nodes of tip and present thereafter — 5R 4/4 on sun-exposed shoots; shaded shoots have less anthocyanin.

*Shape.*—Curved when growing rapidly.

*Apex.*—Normal, triangular.

Leaves:

*Shape.*—Cordiform (heart shaped); inferior lateral sinuses are medium in depth; superior lateral sinuses deep.

*Apex.*—Pointed.

*Base.*—Rounded.

*Margin.*—Teeth irregular.

*Height of teeth on margin* (*average*).—0.58 cm (ranges from 0.2 cm to 1.0 cm; height/width ratio is about 0.54 (ranges from 0.40 to 0.66).

*Shape of teeth on margin.*—Average dentation, slightly convex sides.

*Texture* (*mature leaf*).—Upper surface: Smooth to slightly bullate; glabrous except for slight pubescence on veins Lower surface: Smooth; almost glabrous with short hairs on veins.

*Immature leaf.*—Length: 8.0 cm at 13 days of age, 5$^{th}$ leaf from tip Width: 6.99 cm at 13 days of age, 5$^{th}$ leaf from tip Color, upper surface: 5GY 6/6 Color, lower surface: 5GY 7/10.

*Mature leaf.*—Length: 15.01 cm at 8 weeks of age Width: 13.0 cm at 8 weeks of age Color, upper surface: 5GY 4/8 Color, lower surface: 5GY 6/6.

*Venation.*—Pattern: Upper surface veins are visually distinct due to their lighter color contrasting with interveinal tissue; lower surface veins are raised Color: Upper surface: 2.5GY 7/8 Lower surface: 2.5GY 8/6.

*Petiolar sinus.*—U- shaped.

*Petiole.*—Length: 8.02 cm inches average Diameter: 0.3 cm Color: 2.5GY 8/6.

Floral cluster:

*General description and location.*—Medium-large, often winged; primary clusters positioned on nodes 5 and 6; secondary clusters positioned on nodes 4 to 7.

*Quantity of inflorescences per cluster* (*average*).—435 (ranges from 121 to 927).

*Length* (*average*).—18.16 cm.

*Width* (*average*).—8.86 cm at the shoulder; length of wing is about 11.07 cm.

*Peduncle length* (*average*).—3.28 cm.

*Inflorescences.*—Hermaphroditic.

*Stamens.*—Medium length with tendency to curve outward.

*Anthers.*—Yellowish-brown in center with a light, cream colored border.

*Date of bloom.*—1$^{st}$ bloom on May 6, 2008, 1–2 days later than 'Thompson Seedless'; 85% bloom on May 10, 2008.

*Pollen amount.*—Low to moderate.

*Calyptra.*—Slightly segmented.

*Calyptra color.*—5GY 5/8, becoming lighter, 2.5GY 8/6 at apex.

Fruit:

*Time of year of commercial harvest and shipment.*—Beginning of veraison — Jul. 2, 2008 Harvest — Sep. 9, 2008.

*Cluster* (*primary bunches*).—General size: Medium, average is 0.76 lb in 2008 Length (without peduncle): 20.12 cm Width: 12.85 cm Density: Loose to medium Peduncle length: 3.76 cm Peduncle diameter: 0.5 cm Peduncle color: 2.5GY 7/10 Number of berries per cluster (average): 43 berries Berry: Size: Large, average 8 grams in 2008 Shape: Ellipsoidal to obovoid with tendency to be flattened on the ends Uniformity: Good Brix content: 20.5% Diameter: 2.25 cm Length: 2.60 cm Skin color: 2.5GY 8/6 Pedicel: Length: 1.0 cm Diameter: 0.25 cm Color: 2.5GY 7/10 Strength of attachment to berry: Very good.

*Cluster* (*secondary bunches*).—General size: Small/medium; average is 0.45 lb. in 2008 Length (average without peduncle): 16.46 cm Width (average): 9.83 cm Density: Mostly loose Peduncle length: 3.71 cm Peduncle diameter: 0.5 cm Peduncle color: 2.5GY 7/10 Number of berries per cluster (average): 30 berries Berry: Size: Large; average 7.1 grams in 2008 Shape: Ellipsoidal to obovoid with tendency to be somewhat flattened on the ends Uniformity: Good Brix content: 20.8% Diameter: 2.25 cm Length: 2.58 cm Skin color: 2.5GY 8/6 Pedicel: Length: 1.0 cm Diameter: 0.25 cm Color: 2.5GY 7/10 Strength of attachment to berry: Very good.

Berry flesh:

*Color.*—2.5GY 8/4.

*Juice, color.*—Clear.

*Juice production.*—Low.

*Thickness of skin.*—Medium.

*Flavor.*—Sweet with some floral fruitiness (slight Muscat flavor).

*Fragrance.*—None.

*Texture.*—Firm.

Fruit and seed set:Seed traces are very small and almost not visually detectable and too small to describe and are less than 1 mm in size when present.

Disease and insect resistance: No particular resistance or susceptibility has been observed. Normal disease control practices can be used.

COMPARISON WITH PARENTAL AND COMMERCIAL CULTIVARS

'95–133' differs from the female parent '90–4981' (unpatented) in that '95–133' has green seedless berries, while '90–4981' has red seeded berries.

'95–133' differs from the male parent 'C.G. 88–552' (unpatented) in that '95–133' has green seedless berries, while 'C.G. 88–552' has red seedless berries.

'95–133' differs from the commercial cultivar 'Arrafourteen' (U.S. Plant Pat. No. 18,625) in that '95–133' has green berries, while 'Arrafourteen' has red berries. Additionally, '95–133' has larger berries (about 8 grams in weight per berry), while 'Arrafourteen' has smaller berries (4.7 grams in weight per berry).

'95–133' differs from the commercial cultivar 'Thompson Seedless' (unpatented) in that '95–133' has larger berries than 'Thompson Seedless'.

I claim:

1. A new and distinct cultivar of grapevine plant, as shown and described herein.

* * * * *